(12) United States Patent
Yum

(10) Patent No.: US 7,979,118 B2
(45) Date of Patent: Jul. 12, 2011

(54) LOW FREQUENCY GENERATION POULTICE

(76) Inventor: Hyunjik Yum, Bucheon-si (KR)

( * ) Notice: Subject to any disclaimer, the term of this patent is extended or adjusted under 35 U.S.C. 154(b) by 130 days.

(21) Appl. No.: 12/531,872

(22) PCT Filed: Mar. 19, 2008

(86) PCT No.: PCT/KR2008/001544
§ 371 (c)(1),
(2), (4) Date: Sep. 17, 2009

(87) PCT Pub. No.: WO2008/115001
PCT Pub. Date: Sep. 25, 2008

(65) Prior Publication Data
US 2010/0056984 A1    Mar. 4, 2010

(30) Foreign Application Priority Data
Mar. 20, 2007 (KR) .................. 10-2007-0026977

(51) Int. Cl.
*A61N 1/30* (2006.01)
(52) U.S. Cl. ................... 604/20; 424/449; 607/2; 607/3
(58) Field of Classification Search ................. 604/20; 424/449; 607/2, 3
See application file for complete search history.

(56) References Cited

U.S. PATENT DOCUMENTS

| | | |
|---|---|---|
| 5,578,065 A | 11/1996 | Hattori |
| 6,162,460 A | 12/2000 | Lee |

FOREIGN PATENT DOCUMENTS

| | | |
|---|---|---|
| KR | 10-0245836 | 10/1998 |
| KR | 10-0245835 | 9/1999 |
| KR | 20-0375960 | 3/2005 |
| WO | 01/74445 A1 | 10/2001 |

*Primary Examiner* — Theodore J Stigell
*Assistant Examiner* — Deanna K Hall
(74) *Attorney, Agent, or Firm* — Knobbe Martens Olson & Bear LLP

(57) ABSTRACT

A low frequency generating poultice includes a poultice sheet; a contact fabric that is adhered to a non-medicated surface of the poultice sheet; a release sheet that is attached to a medicated surface of the poultice sheet; a low frequency oscillator; a pair of left and right first through holes; a pair of left and right second through holes that are formed in the poultice sheet, the contact fabric, and the release sheet; and a left clip portion and a right clip portion that have one end fixed to a bottom surface of the low frequency oscillator and the other end passing through the pair of left and right first through holes to be coupled to the poultice sheet through the pair of left and right second through holes and electrically connected to the low frequency oscillator.

5 Claims, 4 Drawing Sheets

[Fig. 1]
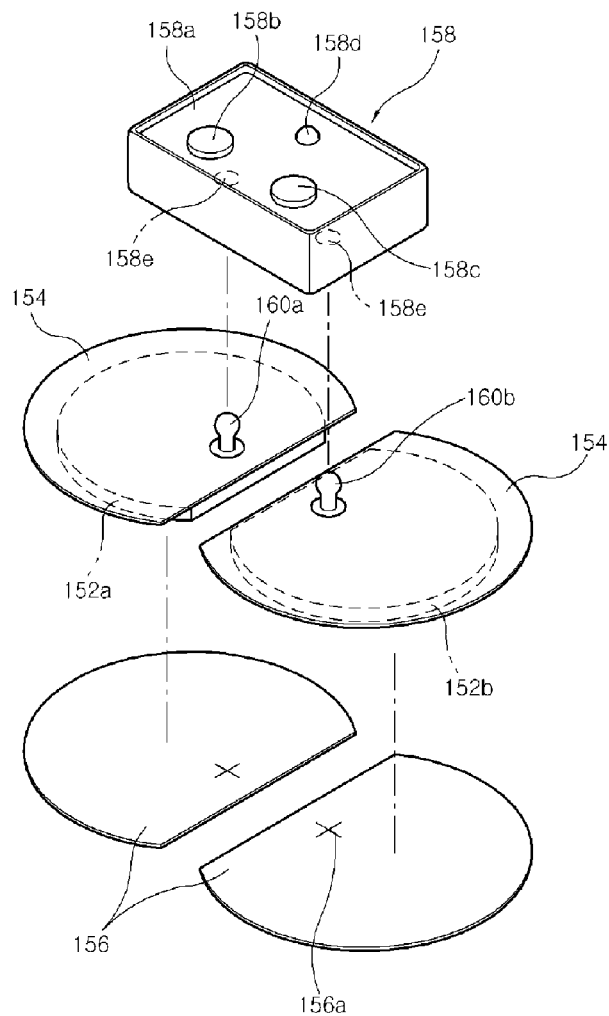
[Fig. 2]
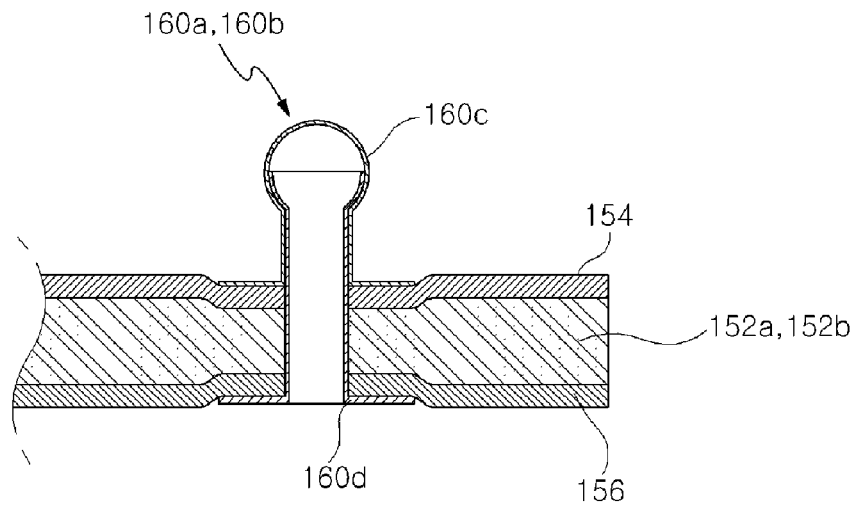

[Fig. 3]
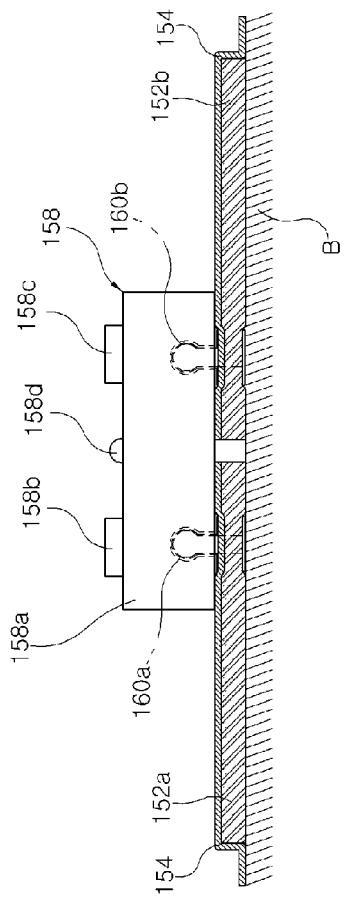
[Fig. 4]
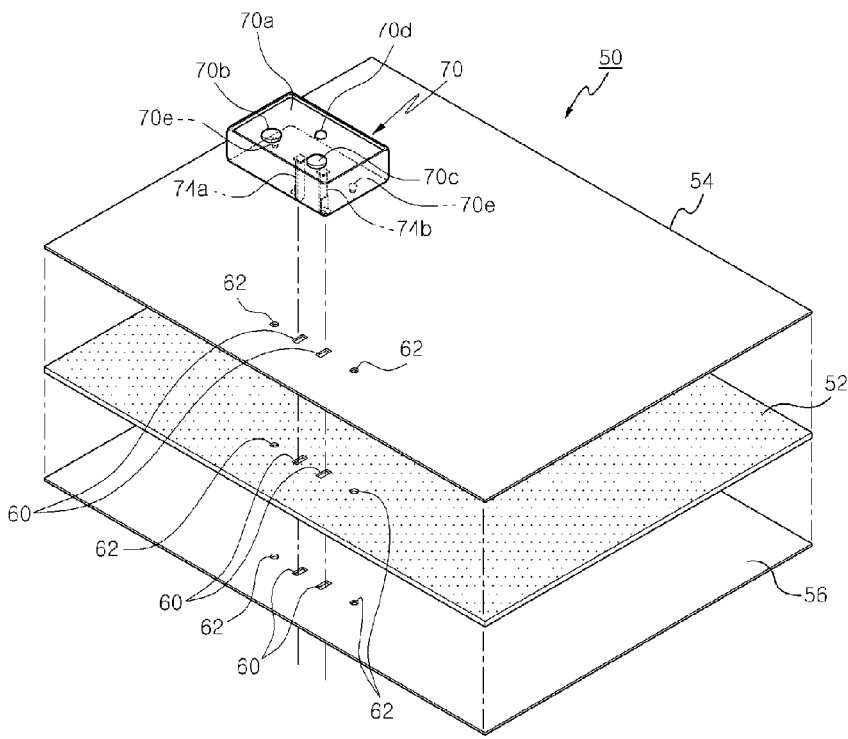

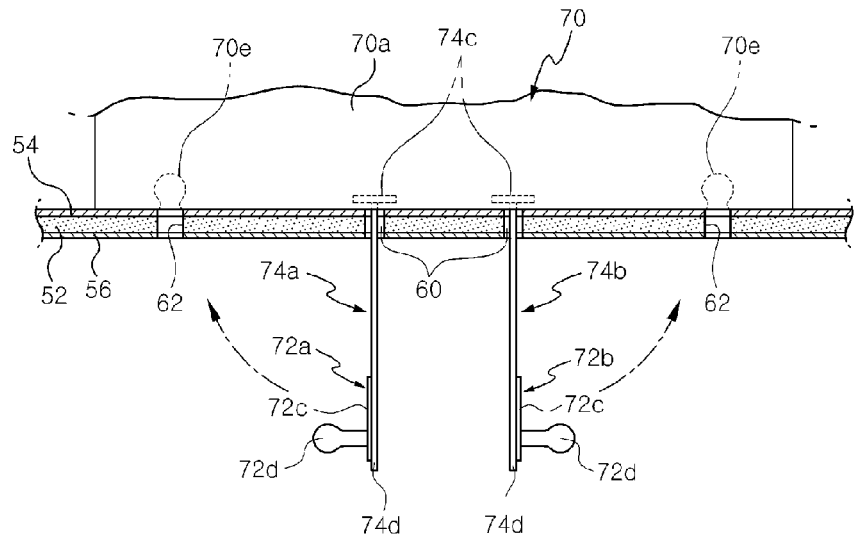
[Fig. 5]
(a)
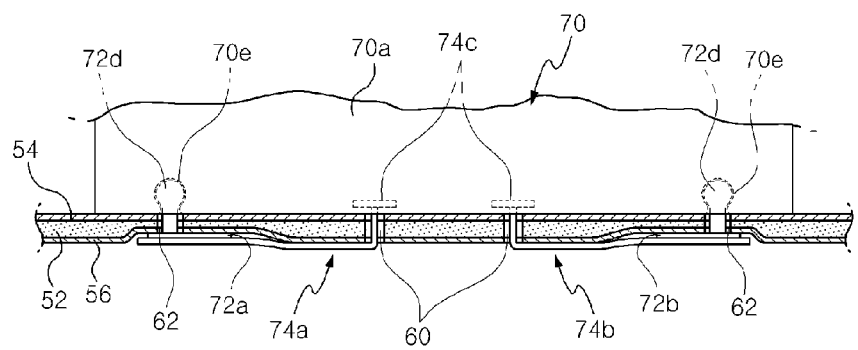
(b)
[Fig. 6]
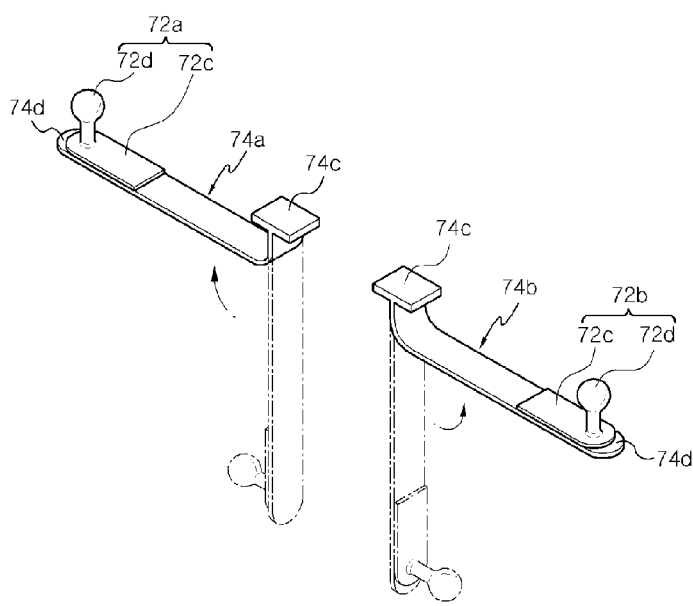

[Fig. 7]
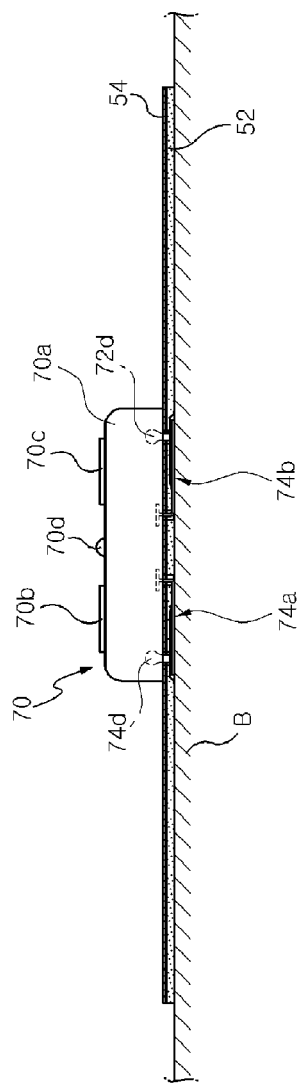
[Fig. 8]
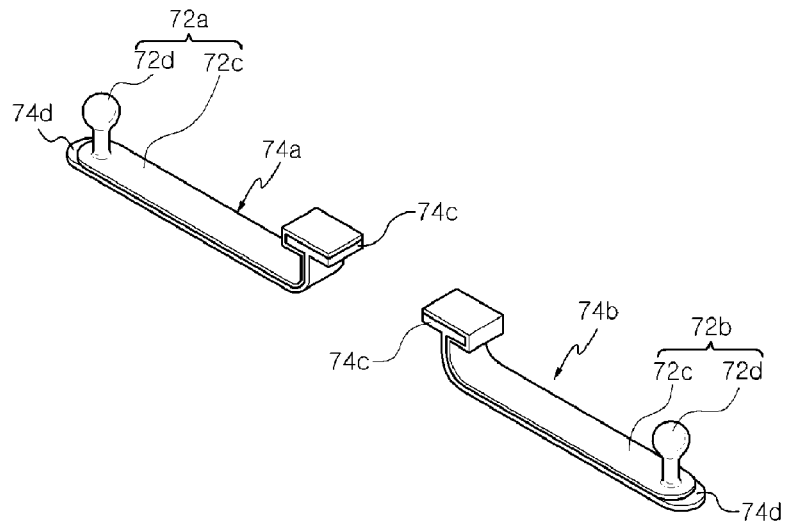

LOW FREQUENCY GENERATION POULTICE

TECHNICAL FIELD

The present invention relates to a low frequency generating poultice (including patch type, cataplasma type, plaster type, puff type, and the like), and more particularly, to a low frequency generating poultice that is adapted to be attached to skin where a bruise, myalgia, arthritis or neuralgia occurs to increase permeation efficiency of medication to hypodermic tissues according to a low frequency effect for quick treatment of pain and further increase a medicinal effect according to physical frequency vibration.

BACKGROUND ART

Generally, a poultice (including patch type, cataplasma type, plaster type, puff type, and the like) is made of fabric where one side thereof is applied with adhesive medication and a poultice sheet is attached with a vinyl release sheet for protection of medication and release in use. The poultice sheet is made of soft material and is resiliently attached to skin.

Therefore, when a user uses the poultice, the user attaches the poultice, from which the release sheet is removed, to the affected part of the skin for a predetermined period of time, such that continuous permeation of medication and action thereof relieve the pain.

However, in the poultice according to the related art, physical treatment is not provided to the affected part and the pain is treated only by a medicinal action from applied medication. For this reason, a treatment effect is decreased and the permeation speed of medication is slow while the permeability of medication considerably lessens over time, which causes the need to change the attached poultice with a new poultice for continued treatment after a predetermined period of time. Further, the period of time during which the poultice is attached to the affected part of the skin having pain is increased, and if the poultice is attached to the skin for a period of time longer than is necessary, skin pores are closed to cause allergies such as itching or erythema on the affected part. As a result, when the user uses the poultice, it is inconvenient to the user, and it is not possible to confirm the medicinal duration of the poultice.

As a physical treatment method in a hospital to increase the treatment effect on the affected part, there is a physical treatment method using a separate low frequency generating device. In this case, however, there is a problem in that a medical fee is increased and an economic burden is laden with a patient due to expensive equipment, and the patient cannot perform self treatment using the low frequency generating device.

Meanwhile, there is a spray gun-typed medication atomizer containing liquid medication therein and having a treatment function similar to that of the poultice. In this case, the atomizer is used for treatment by pressing a button thereon and spraying medication in a container to an affected part. There is however a problem in that it is inconvenient for the user and a medicinal effect is inferior to that of the poultice in terms of duration thereof.

Therefore, there arises a necessity of simplifying treatment while maximizing the treatment effect in a short time in consideration of the fact that most of the muscle or arthralgia patients widely use the poultice (including patch type, cataplasma type, plaster type, and puff type).

To overcome these problems, in the related art, a low frequency generating poultice under Korean Utility Model Registration No. 0375960 (Registration Date: 2005 Feb. 3) has been suggested.

That is, as shown in FIGS. 1 to 3, a low frequency generating poultice 150 according to the related art includes left and right poultice sheets 152a and 152b, a contact fabric 154, a vinyl release sheet 156, a conductive left snap button 160a, a conductive right snap button 160b, and a low frequency oscillator 158. The left and right poultice sheets 152a and 152b contain medication and are opposite to each other with a predetermined gap. The contact fabric 154 is formed to have an area larger than the combined left and right poultice sheets 152a and 152b and is adhered to the non-medicated surfaces (top surfaces) of the left and right poultice sheet 152a and 152b.

The vinyl release sheet 156 is attached to medicated surfaces (bottom surfaces) of the left and right poultice sheets 152a and 152b and a bonding surface of the contact fabric 154 at the edge to simultaneously protect the medicated surfaces and the bonding surface, and is releasable at the time of utilizing thereof. The conductive left snap button 160a simultaneously fixes the contact fabric 154 and the release sheet 156 adhered to an upper portion and a lower portion of the left poultice sheet 152a with the left poultice sheet 152a therebetween by means of riveting and partially protrudes to a top surface of the contact fabric 154, such that a low frequency cathode current flows through the left poultice sheet 152a. The conductive right snap button 160b simultaneously fixes the contact fabric 154 and the release sheet 156 adhered to an upper portion and a lower portion of the right poultice sheet 152b with the right poultice sheet 152b therebetween by means of riveting and partially protrudes to the top surface of the contact fabric 154, such that a low frequency anode current flows through the right poultice sheet 152b. The low frequency oscillator 158 is disposed to be attached to or detached from the left and right snap buttons 160a and 160b and has a pair of left and right snap holes 158e through which that a low frequency cathode current and a low frequency anode current flow.

That is, the contact fabric 154 is formed to have an area larger than the combined left and right poultice sheets 152a and 152b and to be divided into the left and right portions, such that the contact fabric 154 has a central portion adhered to non-medicated surfaces (top surfaces) of the left and right poultice sheets 152a and 152b and an edge adhered to the affected part (B) of the user.

The release sheet 156 is formed to have an area larger than the combined left and right poultice sheets 152a and 152b and to be divided into the left and right portions, such that the release sheet 156 has a central portion adhered to the non-medicated surfaces (bottom surfaces) of the left and right poultice sheets 152a and 152b and an edge adhered to a bottom surface of the contact fabric 154 at an edge thereof.

Cross-shaped cut lines 156a are formed at one side of the release sheet 156, such that the release sheet 156 is easily separated from the left and right snap buttons 160a and 160b when separating the release sheet 156a in a state where the contact fabric 154, the left and right poultice sheets 152a and 152b, and the release sheet 156 are simultaneously riveted and fixed by means of the left and right snap buttons 160a and 160b.

Meanwhile, the low frequency oscillator 158 has a body 158a and an on/off button 158b, an up/down button 158c, and a signal unit 158d that are installed on a top surface of the body 158a at the predetermined intervals. In the body 158a, a battery and electronic components (not shown) are incorporated. The left and right snap buttons 160a and 160b are easily attached to or detached from the bottom surface of the body 158a. In the bottom surface 158a, a pair of left and right snap holes 158e that are electrically connected to the electronic components (not shown) in the body 158a are formed, such that a low frequency cathode current and a low frequency anode current flow through the pair of left and right snap holes 158e when the left and right snap buttons 160a and 160b are connected to the body 158a.

As shown in FIG. 2, each of the left and right snap buttons 160a and 160b includes a first conductor 160c and a second conductor 160d. The first conductor 160c is adhered to one side of the top surface of the contact fabric 154 so as to be attached to or detached from each of the pair of left and right snap holes 158e of the low frequency oscillator 158. The second conductor 160d has one end that sequentially penetrates the release sheet 156, the left poultice sheet 152a or the right poultice sheet 152b, and the contact fabric 154, and is pressurized into and coupled to the first conductor 160c.

However, in the low frequency generating poultice 150 according to the related art that has the above-described structure, the left and right poultice sheets 152a and 152b are separately manufactured such that they are symmetrical to each other at the left and right sides and the contact fabric 154 and the release sheet 156 are separately manufactured to correspond to the left and right poultice sheets 152a and 152b. As such, an additional process is required because the poultice sheets 152a and 152b, the contact fabric 154, and the release sheet 156 are manufactured to be divided into the left and right sides, which results in increasing manufacturing costs. The low frequency oscillator 158 and poultice sheets 152a and 152b are bonded to each other at the central portion of the low frequency oscillator 158. For this reason, if the motion or weak impact is applied to the edge of the low frequency oscillator 158, this causes the low frequency oscillator 158 to be easily separated and omitted from the poultice sheets 152a and 152b, which results in lowering the reliability of the product for the consumer.

Since the second conductor 160d directly comes into contact with the affected part (B) of the user, if the current stimulates the skin, and a strong vibration mode may injure the user.

In the manufacturing steps, since the left and right poultice sheets 152a and 152b and the contact fabric 154 are riveted and fixed for each pair at the inner sides of the central portions thereof by means of the left and right snap buttons 160a and 160b, when the plurality of refillable poultice sheets 152a and 152b are packed, the volume of packing paper is increased due to the snap buttons 160a and 160b. Further, since the snap buttons 160a and 160b should be fixed to the plurality of poultice sheets 152a and 152b, due to costs of components such as the snap buttons 160a and 160b and the second conductor 160d and assembly costs thereof, manufacturing costs are increased. Since the snap buttons 160a and 160b protrude, while products are stored or circulated, the packing paper and the poultice 150 are damaged or the snap buttons 160a and 160b and the second conductor 160d are damaged, which makes it impossible to use the products.

Further, since the snap buttons 160a and 160b are fixed to the centers of the poultice sheets 152a and 152b and the second conductor 160d is located occupying a large area thereon, in the case where the poultice is attached to the affected part using a general attaching method in which the central portions of the poultice sheets 152a and 152b are attached to the center of the affected part (B) having severe pain, the affected part is blocked or the poultice sheets 152a and 152b are attached to the affected part to be inclined to one side due to an area occupied by the snap buttons 160a and 160b and the second conductor 160d. As a result, it is impossible to concentrate medication components from the poultice sheets 152a and 152b on the affected part.

DISCLOSURE OF INVENTION

Technical Problem

Accordingly, the present invention has been made to solve the problems in the related art, and it is an object of the present invention to provide a low frequency generating poultice that is capable of providing convenience for a user while decreasing a manufacturing cost, decreasing the volume of packing paper, preventing products from being damaged, stably coupling a low frequency oscillator and a poultice sheet, and concentrating a low frequency component and a medication component from the poultice sheet on an affected part having severe pain while protecting the skin of the user.

Technical Solution

In order to achieve the above-described object, according to an embodiment of the present invention, a low frequency generating poultice includes a poultice sheet; a contact fabric that is adhered to a non-medicated surface (top surface) of the poultice sheet; a release sheet that is attached to a medicated surface (bottom surface) of the poultice sheet; a low frequency oscillator that generates a low frequency; a pair of left and right first through holes that are formed opposite to each other at the edges of one side of the poultice sheet, the contact fabric, and the release sheet at predetermined intervals; a pair of left and right second through holes that are formed in the poultice sheet, the contact fabric, and the release sheet so as to be opposite to the outside of the pair of left and right first through holes at predetermined intervals from the pair of left and right first through holes; and a left clip portion and a right clip portion that have one end fixed to a bottom surface of the low frequency oscillator and the other end passing through the pair of left and right first through holes to be coupled to the poultice sheet through the pair of left and right second through holes and electrically connected to the low frequency oscillator, and have a cathode terminal and an anode terminal, respectively, such that a low frequency cathode current and a low frequency anode current flow through the poultice sheet.

As another embodiment, the pair of left and right first through holes may be cut in a slit shape, such that the left and right clip portions pass through the pair of left and right first through holes.

As another embodiment, the pair of left and right second through holes may be cut in a circular shape, such that snap-shaped portions of the cathode terminal and the anode terminal pass through the poultice sheet and are electrically connected to the low frequency oscillator.

As another embodiment, the cathode and anode terminals may include a pair of left and right connection plates formed at one side thereof and a pair of left and right connection protrusions formed at the other side thereof. The pair of left and right connection plates may be respectively coupled to the left and right clip portions and adhered to a bottom surface of the poultice sheet, and the pair of left and right connection protrusions may be connected to a pair of left and right connection grooves formed on a bottom surface of the low frequency oscillator so as to be attached to or detached from the pair of left and right connection grooves by a snap and perform a control operation such that the low frequency cathode current and the low frequency anode current flow through the poultice sheet.

As another embodiment, the left and right clip portions as nonconductors may include a pair of left and right coupling portions formed at one side thereof and a pair of left and right flat portions formed at the other side thereof. The pair of left and right coupling portions may protrude to be fixed to a bottom surface of a body of the low frequency oscillator, and the pair of left and right flat portions may be formed such that the cathode and anode terminals are fixed thereon.

Advantageous Effects

The low frequency generating poultice according to the present invention has the following effect. The poultice sheet, the contact fabric, and the release sheet can be integrated as one sheet without dividing them into the left and right sides at the time of producing products, and the accessories, such as the snap buttons and the second conductor, are not bonded to the contact fabric, the poultice sheet, and the release sheet. Further, the low frequency can be transmitted through the connection grooves installed in the low frequency oscillator. Therefore, when using the low frequency generating poultice, it is convenient for the user, the manufacturing cost can be decreased, the volume of packing paper can be decreased, products can be prevented from being damaged, a low frequency component and a medication component from the poultice sheet can be concentrated on an affected part having severe pain while protecting the skin of the user, and the low frequency oscillator and the poultice sheet can be stably coupled to each other.

BRIEF DESCRIPTION OF THE DRAWINGS

FIG. 1 is an exploded perspective view illustrating a low frequency generating poultice according to the related art.

FIG. 2 is an enlarged cross-sectional view illustrating a fixed state of snap buttons according to the related art.

FIG. 3 is a lateral cross-sectional view illustrating a utilization state shown in FIG. 2.

FIG. 4 is an exploded perspective view illustrating a low frequency generating poultice according to a first embodiment of the present invention.

FIGS. 5A and 5B are partially enlarged cross-sectional views illustrating an assembly sequence according to a first embodiment of the present invention.

FIG. 6 is a perspective view illustrating left and right clip portions to which cathode and anode terminals are coupled in accordance with an embodiment of the present invention.

FIG. 7 is a diagram illustrating a utilization state of a low frequency generating poultice according to a first embodiment of the present invention.

FIG. 8 is a lateral view illustrating a low frequency oscillator according to a second embodiment of the present invention.

BEST MODE FOR CARRYING OUT THE INVENTION

First Embodiment

Hereinafter, a first embodiment of the present invention will be described in detail with reference to FIGS. 4 to 6.

As shown in FIG. 4, a low frequency generating poultice 50 according to a first embodiment of the present invention includes a poultice sheet 52, a contact fabric 54, a vinyl release sheet 56, a pair of left and right first through holes 60, a pair of left and right second through holes 62, a low frequency oscillator 70, and a left clip portion 74a and a right clip portion 74b. The poultice sheet 52 is applied with skin-adhesive medicine and the contact fabric 54 is adhered to a non-medicated surface (top surface) of the poultice sheet 52. The vinyl release sheet 56 is formed to have an area corresponding to an area of the poultice sheet 52, adhered to a medicated surface (bottom surface) of the poultice sheet 52, and releasable at the time of utilization. The pair of left and right first through holes 60 are formed opposite to each other at edges of the poultice sheet 52, the contact fabric 54, and the vinyl release sheet 56 at one side thereof at the predetermined intervals. The pair of left and right second through holes 62 are formed in the poultice sheet 52, the contact fabric 54, and the vinyl release sheet 56 to be opposite to the outside of the pair of left and right first through holes 60 at the predetermined intervals with the pair of left and right first through holes 60. The low frequency oscillator 70 is located at a top surface of the contact fabric 54 and changes its mode into various vibration modes at the time of an ON operation to generate a low frequency. The left clip portion 74a and the right clip portion 74b have one end fixed to a bottom surface of the low frequency oscillator 70 and the other end coupled to the poultice sheet 52 through the pair of left and right first through holes 60 and the pair of left and right second through holes 62 and electrically connected to the low frequency oscillator 70, and has a cathode terminal 72a and an anode terminal 72b, respectively, such that a low frequency cathode current and a low frequency anode current flow through the poultice sheet 52.

That is, the pair of left and right first through holes 60 are preferably cut in a slit shape such that the left and right clip portions 74a and 74b can easily penetrate the pair of left and right first through holes 60.

The pair of left and right second through holes 62 are preferably cut in a circular shape such that snap-shaped portions of the cathode terminal 72a and the anode terminal 72b penetrate the poultice sheet 52 and are electrically connected to the low frequency oscillator 70.

At this time, the pair of left and right first through holes 60 and the pair of left and right second through holes 62 are punched to be simultaneously cut having the same interval and size in a state where the poultice sheet 52, the contact fabric 54, and the release sheet 56 are laminated at the time of manufacturing products.

The low frequency oscillator 70 includes a body 70a and an on/off button 70b, an up/down button 70c, and a signal unit 70d that are formed on a top surface of the body 70a with a predetermined gap. In the body 70a, a battery and electronic components (not shown) are incorporated. In a bottom surface of the body 70a, a pair of left and right connection grooves 70e that are electrically connected to the electronic components (not shown) in the body 70a are formed such that a low frequency cathode current and a low frequency anode current flow when the cathode terminal 72a and the anode terminal 72b are connected by a snap.

As shown in FIG. 6, the cathode and anode terminals 72a and 72b include a plurality of left and right connection plates 72c and a pair of left and right connection protrusions 72d formed at the other side. The pair of left and right connection plates 72c are respectively coupled to the left and right clip portions 74a and 74b and adhered to the bottom surface of the poultice sheet 52. The pair of left and right connection protrusions 72d are connected to the pair of left and right connection grooves 70e of the low frequency oscillator 70 by a snap to be attached to or detached from the pair of left and right connection grooves 70e and performs a control operation such that the low frequency cathode current and the low frequency anode current flow through the poultice sheet 52.

The left and right clip portions 74a and 74b as thin non-conductors having elasticity as shown in FIG. 6 includes a pair of left and right coupling portions 74c formed at one side and a pair of left and right flat portions 74d formed at the other side. The pair of left and right coupling portions 74c protrude to be fixed to the bottom surface of the body 70a of the low frequency oscillator 70. The pair of left and right flat portions 74d are formed such that the cathode and anode terminals 72a and 72b are fixed thereon.

Next, the function and effect of the first embodiment of the present invention that has the above-described structure will be described.

In order to use the low frequency generating poultice 50, the user assembles the low frequency oscillator 70 mounted with the left and right clip portions 74a and 74b in the poultice sheet 52 in which the pair of left and right first through holes 60 and the pair of left and right second through holes 62 are formed and the contact fabric 54 and the release sheet 56 are attached to the top surface and the bottom surface.

That is, the left and right clip portions 74a and 74b that are fixed to the bottom surface of the low frequency oscillator 70 are located toward the upper side of the contact fabric 54. As shown in FIG. 5A, the left and right clip portions 74a and 74b are respectively inserted into the pair of left and right first through holes 60 that are simultaneously cut in the contact fabric 54, the poultice sheet 52, and the release sheet 56.

At this time, since the pair of left and right first through holes 60 are formed to correspond to the thickness of the left and right clip portions 74a and 74b, the cathode terminal 72a and the anode terminal 72b that are respectively coupled to the flat portions 74d at the ends of the left and right clip portions 74a and 74b easily pass through the pair of left and right first through holes 60 and are located below the bottom surface of the release sheet 56.

In this state, if the left and right clip portions 74a and 74b are lifted toward the release sheet 56, the left and right clip portions 74a and 74b are bent due to elasticity, and the connection protrusions 72d of the cathode terminal 72a and the anode terminal 72b that are coupled to the top surfaces of the flat portions 74d at the ends thereof are automatically aligned with the pair of left and right second through holes 62.

At this time, if the flat portions 74d are pressed toward the release sheet 56, the connection protrusions 72d pass through the pair of left and right second through holes that connect the second through holes 62 that connect the release sheet 56, the poultice sheet 52, and the contact fabric 54 by means of a pressing force and are inserted into the pair of left and right connection grooves 70e that are formed in the bottom surface of the low frequency oscillator 70 at the side of the body 70a. As a result, the cathode terminal 72a and the anode terminal 72b are electrically connected to the low frequency oscillator 70, as shown in FIG. 5B.

In this state, if the release sheet 56 is released from the medicated surface (bottom surface) of the poultice sheet 52, the connection plates 72c that extends to be integrated with the other sides (bottom surfaces) of the connection protrusions 72d directly adhere to the medicated surface of the poultice sheet 52, such that the low frequency currents flow through it. The components that are adhered to the medicated surface of the poultice sheet 52 are closely adhered to the connection plates 72c.

In the state of separating the release sheet 56 attached to the medicated surface (bottom surface) of the poultice sheet 52, if the user attaches the poultice sheet 52 to the affected part (B) having a pain as shown in FIG. 7, the poultice sheet 52 is firmly attached to the affected part (B) of the user by an adhesive component applied to the medicated surface of the poultice sheet 52 at the lower side, and the poultice sheet 52 is firmly maintained at the affected part (B) of the user without being separated from the affected part.

In this state, the user presses the on/off button 70b of the low frequency oscillator 70 that is installed on the contact fabric 54 to perform an ON operation, and then presses the up/down button 70c to select a vibration mode. Since the vibration mode is constructed in a circuit form to be changed into at least five steps, a desired section of a vibration mode is selectively adjusted whenever the user presses the up/down button 70c.

Accordingly, when the low frequency cathode and anode currents are generated according to the operation of the low frequency oscillator 70, the low frequency cathode and anode currents flow through the poultice sheet 52 through the connection protrusion 72d of the cathode terminal 72a and the connection protrusion 72d of the anode terminal 72b that are connected to the connection grooves 70e of the low frequency oscillator 70 and permeate into the hypodermic tissue of the skin, thereby helping to carry the medicated component from the poultice sheet 52 into the affected part (B) quickly and deeply.

That is, the low frequency cathode currents transmitted from the cathode terminal 72a to the affected part (B) through the left side of the poultice sheet 52 are electrically connected to the low frequency anode currents transmitted from the anode terminal 72b to the affected part (B) through the right side of the poultice sheet 52, and a medical action of the low frequency is activated. As a result, the medicated components from the poultice sheet 52 starts to deeply permeate into the affected part (B).

As such, a medicated component from the poultice sheet 52 and another medicated component from direct current generated from the low frequency simultaneously permeate into the affected part (B) to vitalize the medical action, and physical therapy using low frequency vibration provides a quicker relief of pain for the affected part (B) for quicker recovery.

Meanwhile, the battery in the low frequency oscillator 70 has enough capacity to enable a plurality of poultice sheets 52 to be changed after a predetermined period of time, such that, when the medicated component of the poultice sheet 52 is removed after the predetermined period of time, the poultice sheet 52 and the contact fabric 54 may be separated from the cathode and anode terminals 72a and 72b and the low frequency oscillator 70 in the reverse order of the above-described operation and then removed, and a new poultice sheet 52 and a new contact fabric 54 replace the old poultice 52 and the old contact fabric 54.

Accordingly, the low frequency generating poultice 50 according to the present invention can integrate the poultice sheet 52, the contact fabric 54, and the release sheet 56 as one sheet without dividing them into the left and right sides at the time of producing the products. As a result, the manufacturing costs can be decreased, and a consumer can easily and conveniently couple the low frequency oscillator 70 to or separate the low frequency oscillator 70 from the poultice sheet 52.

The components that include the poultice sheet 52, the contact fabric 54, and the release sheet 56 have the structure in which, in the manufacturing steps, accessories (for example, snap buttons and second conductor in the related art) are not attached to the components and only the first and second through holes 60 and 62 are simultaneously cut and processed in predetermined sizes. It is possible to reduce the manufacturing costs due to coupling of the accessories such as the snap buttons and the second conductor. When the plurality of refillable poultice sheets 52, the contact fabric 54, and the release sheet 56 are packed in large quantities, the volume thereof can be reduced, the storage and circulation are easy, and the products can be prevented from being destroyed in advance.

Since the poultice sheet 52 is coupled to the low frequency oscillator 70 at the edge of the poultice sheet 52 apart from the central portion thereof, when the poultice sheet 52 is attached to the center of the affected part (B) having severe pain, the medicated component from the poultice sheet 52 and the low frequency component from the low frequency oscillator 70 are concentrated, thereby vitalizing the medical action.

Since the left and right clip portions 74a and 74b that are coupled to the cathode and anode terminals 72a and 72b are nonconductors, the cathode and anode terminals 72a and 72b do not directly come into contact with the affected part (B) of the user. As a result, it is possible to prevent current generated from the low frequency oscillator 70 from directly flowing through the affected part (B), thereby protecting the skin of the user.

Second Embodiment

A second embodiment of the present invention will be described in detail with reference to FIG. 8.

For reference, FIG. 8 shows the second embodiment of the present invention, but the same structures as those of the first embodiment of the present invention are denoted by the same names and reference numerals, and the detailed description thereof will be omitted.

In a low frequency generating poultice 50 according to the second embodiment of the present invention, connection plates 72c of a cathode terminal 72a and an anode terminal 72b may extend such that the connection plates 72c reach from ends of coupling portions 74c of left and right clip portions 74a and 74b to ends of flat portions 74d, as shown in FIG. 8.

That is, the structure change is made such that the ends of the connection plates 72c of the cathode terminal 72a and the anode terminal 72b that extend to the coupling portions 74c are electrically connected to electronic components (not shown) in a low frequency oscillator 70, and a low frequency does not pass through a pair of left and right connection grooves 70e at the side of the bottom surface of the low frequency oscillator 70. The connection plates 72c may be constructed such that the connection plates 72c are coupled to or separated from connection protrusions 72d the cathode terminal 72a and the anode terminal 72b by a snap.

Although the exemplary embodiments are described, it should be understood that the present invention is not limited by the exemplary embodiments. Accordingly, it will be apparent to those skilled in the art that various modifications and changes can be made without departing from the scope and spirit of the present invention and the present invention includes the various modifications and changes.

The invention claimed is:

1. A low frequency generating poultice comprising:
a poultice sheet;
a contact fabric that is adhered to a non-medicated surface (top surface) of the poultice sheet;
a release sheet that is attached to a medicated surface (bottom surface) of the poultice sheet;
a low frequency oscillator that generates a low frequency;
a pair of left and right first through holes that are formed opposite to each other at the edges of one side of the poultice sheet, the contact fabric, and the release sheet at predetermined intervals;
a pair of left and right second through holes that are formed in the poultice sheet, the contact fabric, and the release sheet so as to be opposite to the outside of the pair of left and right first through holes at predetermined intervals from the pair of left and right first through holes; and
a left clip portion and a right clip portion that have one end fixed to a bottom surface of the low frequency oscillator and the other end passing through the pair of left and right first through holes to be coupled to the poultice sheet through the pair of left and right second through holes and electrically connected to the low frequency oscillator, and have a cathode terminal and an anode terminal, respectively, such that a low frequency cathode current and a low frequency anode current flow through the poultice sheet.

2. The low frequency generating poultice of claim 1, wherein the pair of left and right first through holes are cut in a slit shape, such that the left and right clip portions pass through the pair of left and right first through holes.

3. The low frequency generating poultice of claim 1, wherein the pair of left and right second through holes are cut in a circular shape, such that snap-shaped portions of the cathode terminal and the anode terminal pass through the poultice sheet and are electrically connected to the low frequency oscillator.

4. The low frequency generating poultice of claim 1, wherein the cathode and anode terminals include a pair of left and right connection plates formed at one side thereof and a pair of left and right connection protrusions formed at the other side thereof, and the pair of left and right connection plates are respectively coupled to the left and right clip portions and adhered to a bottom surface of the poultice sheet, and the pair of left and right connection protrusions are connected to a pair of left and right connection grooves formed on a bottom surface of the low frequency oscillator so as to be attached to or detached from the pair of left and right connection grooves by a snap and perform a control operation such that the low frequency cathode current and the low frequency anode current flow through the poultice sheet.

5. The low frequency generating poultice of claim 1, wherein the left and right clip portions as nonconductors include a pair of left and right coupling portions formed at one side thereof and a pair of left and right flat portions formed at the other side thereof, and the pair of left and right coupling portions protrude to be fixed to a bottom surface of a body of the low frequency oscillator, and the pair of left and right flat portions are formed such that the cathode and anode terminals are fixed thereon.

* * * * *